(12) United States Patent
Dasgupta et al.

(10) Patent No.: US 9,506,882 B2
(45) Date of Patent: Nov. 29, 2016

(54) PORTABLE FLUOROSCOPY SYSTEM WITH SPATIO-TEMPORAL FILTERING

(75) Inventors: Udayan Dasgupta, Bangalore (IN); Murtaza Ali, Plano, TX (US)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 691 days.

(21) Appl. No.: 13/352,865

(22) Filed: Jan. 18, 2012

(65) Prior Publication Data

US 2012/0183196 A1 Jul. 19, 2012

Related U.S. Application Data

(60) Provisional application No. 61/433,831, filed on Jan. 18, 2011.

(51) Int. Cl.
*G06K 9/00* (2006.01)
*G01N 23/223* (2006.01)
*G06T 1/20* (2006.01)
*G06T 5/00* (2006.01)

(52) U.S. Cl.
CPC .............. *G01N 23/223* (2013.01); *G06T 1/20* (2013.01); *G06T 5/004* (2013.01); *G01N 2223/076* (2013.01); *G06T 2207/10121* (2013.01); *G06T 2207/20012* (2013.01); *G06T 2207/20182* (2013.01); *G06T 2207/30021* (2013.01); *G06T 2207/30101* (2013.01)

(58) Field of Classification Search
CPC combination set(s) only.
See application file for complete search history.

(56) References Cited

U.S. PATENT DOCUMENTS

| | | | |
|---|---|---|---|
| 6,204,891 B1* | 3/2001 | Florent | 348/616 |
| 6,574,300 B1* | 6/2003 | Florent et al. | 378/19 |
| 7,379,623 B2* | 5/2008 | Rudolph | 382/293 |
| 8,488,849 B2* | 7/2013 | Hu et al. | 382/128 |
| 8,565,533 B1* | 10/2013 | Keithley et al. | 382/205 |
| 2004/0131276 A1* | 7/2004 | Hudson | 382/276 |
| 2006/0056725 A1* | 3/2006 | Keithley et al. | 382/275 |
| 2006/0206743 A1* | 9/2006 | Chang et al. | 713/600 |
| 2008/0288953 A1* | 11/2008 | Ando et al. | 718/106 |
| 2013/0129176 A1* | 5/2013 | Hu et al. | 382/131 |
| 2014/0046186 A1* | 2/2014 | Mauldin et al. | 600/443 |

OTHER PUBLICATIONS

Richard Aufrichtig et al, "Spatio-Temporal X-ray Fluoroscopy Filtering using Object Detection", IEEE Proceedings in Cardiology 1993, London, United Kingdom, Sep. 5-8, 1993, pp. 587-590.
Richard Aufrichtig and David L. Wilson, "X-Ray Fluoroscoopy Spatio-Temporal Filtering with Object Detection", IEEE Transactions on Medical Imaging, vol. 14, No. 4, Dec. 1995, pp. 733-746.
Gert Schoonenberg et al, "Adaptive Spatial-Temporal Filtering Applied to X-Ray Fluoroscopy Angiography", Medical Imaging (Continued)

*Primary Examiner* — Randolph I Chu
(74) *Attorney, Agent, or Firm* — Tuenlap D. Chan; Frank D. Cimino

(57) ABSTRACT

A system for processing real-time fluoroscopy image sequences. A first image frame is loaded into an upper level memory of a hierarchical memory system that is coupled to at least one processing core. The first image frame is processed with an object detection filter to form a likelihood image frame. The first image frame and the likelihood image frame is spatially filtered using a spatial filter look up table (LUT) stored in an L1 level memory of the processing core. The likelihood image frame is temporally filtering using a temporal filter LUT stored in the L1 level memory.

19 Claims, 9 Drawing Sheets

(56) References Cited

OTHER PUBLICATIONS

2005: Visualization, Image-Guided Procedures, and Display, Proc. of SPIE, vol. 5744, Feb. 15, 2005, Bellingham, WA, pp. 870-878.
Marc Hensel et al, "Last Filter for Artifact-Free Noise Reduction of Fluoroscopic Sequences in Real Time", Bildverarbeitung fur die Medizin 2006: Algorithmen, Systeme, Anwendungen, Springer, 2006 (ISBN 3-540-32136-5). Proceedings BVM 2006, Hamburg, Germany, Mar. 19-21, 2006, pp. 16-20.
Marc Hensel et al, "Rea-Time Denoising of Medical X-Ray Image Sequences: Three Entirely Different Approaches", ICIAR 2006, LNCS 4142, Springer-Verlag, Berlin, Heidelberg, 2006, pp. 479-490.
Zhou Wang and Alan C. Bovik, "Mean Squared Error: Love It of Leave It?" IEEE Signal Processing Magazine, Jan. 2009, pp. 98-117.
Udayan Dasgupta et al, "Efficient Implementations of Ultrasound Color Doppler Algorithms on VLIW Architectures", Medical Imaging 2009: Ultrasonic Imaging and Signal Processing, Proc. of SPIE, vol. 7265, Feb. 8, 2009, Lake Buena Vista, FL, pp. 1-12.
Elana Granston, "Hand-Tuning Loops and Control code on the TMS320C6000", Texas Instruments Incorporated, Application Report SPRA666, Aug. 2006, pp. 1-54.
"TMS320C6472 Fixed-Point Digital Signal Processor", Texas Instruments Incorporated, TMS320C6472, SPRS612G, Jun. 2009, pp. 1-269.
Udayan Dasgupta and Murtaza Ali, "Mapping Spatio-Temporal Filtering Algorithms used in Fluoroscopy to Single core and Multi-core DSP architectures", Medical Imaging 2011: Image Processing, Proc. of SPIE, vol. 7962, Feb. 12-17, 2011, Lake Buena Vista, FL, pp. 1-11.

* cited by examiner

PORTABLE FLUOROSCOPY SYSTEM WITH SPATIO-TEMPORAL FILTERING

CLAIM OF PRIORITY UNDER 35 U.S.C. 119(e)

The present application claims priority to and incorporates by reference U.S. Provisional Application No. 61/433,831 filed Jan. 18, 2011, entitled "Mapping Spatio-Temporal Filtering Algorithms used in Fluoroscopy to Single core and Multi-core DSP Architectures."

FIELD OF THE INVENTION

This invention generally relates to spatio-temporal filters and in particular to processing fluoroscopy images with spatio-temporal filters in a portable system using single core or multi-core digital signal processors.

BACKGROUND

Low dose X-ray image sequences, as obtained in fluoroscopy, exhibit high levels of noise that must be suppressed in real-time, while preserving diagnostic structures. Multi-step adaptive filtering approaches, often involving spatio-temporal filters, are typically used to achieve this goal.

Fluoroscopy involves exposing the subject to X-rays and capturing a sequence of images, to aid the physician during surgery or diagnosis. The advantages of real-time imaging and the freedom to freely position the X-ray field during examination makes fluoroscopy a very powerful diagnostic tool. However, due to the length of the fluoroscopic examinations, the exposure rate must be kept much lower than in common radiography, resulting in images that suffer from higher levels of quantum noise than ordinary radiographs. Also typical medical devices like catheters and guide-wires tend to have low contrast and are often difficult to distinguish from the background. These noisy images are then "cleaned" up using sophisticated filtering algorithms which would suppress the noise, but preserve and enhance the features of interest.

Barium studies to investigate the functioning of the gastrointestinal tract, orthopedic surgery for fracture correction and placement of metalwork, studies to detect problems in joint functioning, and angiography and catheter insertion are some of the applications of fluoroscopy. The length of the exams, the exposure rate, the diagnostic features of interest and the image enhancement algorithms, all vary widely across the applications.

The broad classes of algorithms used in these systems include contrast enhancement and spatial and temporal processing algorithms. Typically the spatial filters used in fluoroscopy need to be edge-preserving, while the temporal filters need to ensure that motion does not cause blurring or trailing artifacts. Spatio-temporal filtering attempts to combine the best of both approaches by using spatially filtered outputs if the pixel is affected by motion and temporally filtered outputs if the pixel is static. Some of these schemes may use additional steps to locate and enhance low-contrast objects of interest. The strength of these filters may be adapted using local statistics, object boundaries and motion estimates. They may try to detect application-specific structures, like catheters for angiography procedures. These algorithms often use images with sizes up to 1024×1024 pixels and support frame rates up to 30 frames per sec—thereby creating a need for high performance computational platforms. Spatio-temporal filtering approaches used in fluoroscopy are described in more detail in Richard Aufrichtig and D. L. Wilson, "X-Ray Fluoroscopy Spatio-Temporal Filtering with Object Detection", IEEE Transactions on Medical Imaging, Vol. 14, No. 4, December 1995, pp. 773-746, which is incorporated by reference herein, and Gert Schoonenberg et. al, "Adaptive spatial-temporal filtering applied to x-ray fluoroscopy angiography", Proceedings of SPIE Vol. 5744, Medical Imaging 2005, for example.

BRIEF DESCRIPTION OF THE DRAWINGS

Particular embodiments in accordance with the invention will now be described, by way of example only, and with reference to the accompanying drawings.

Figure 1:
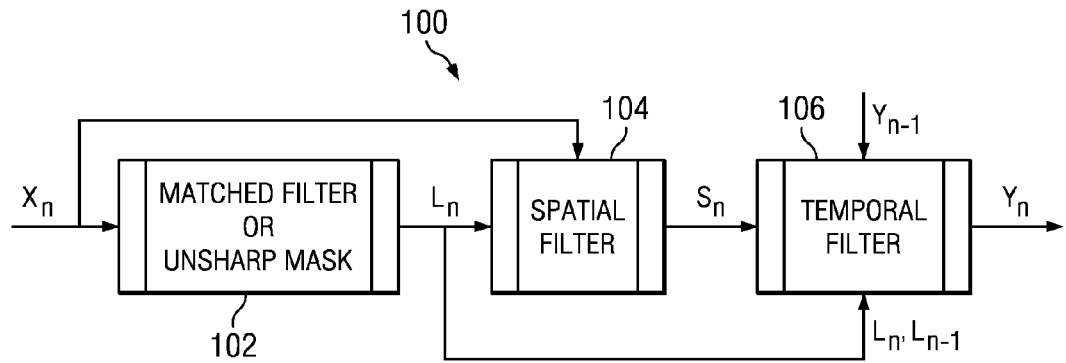
FIGS. 1-2 are flow diagrams illustrating spatio-temporal filtering schemes with object detection.

Other features of the present embodiments will be apparent from the accompanying drawings and from the detailed description that follows.

DETAILED DESCRIPTION OF EMBODIMENTS OF THE INVENTION

Specific embodiments of the invention will now be described in detail with reference to the accompanying figures. Like elements in the various figures are denoted by like reference numerals for consistency. In the following detailed description of embodiments of the invention, numerous specific details are set forth in order to provide a more thorough understanding of the invention. This invention may, however, be embodied in many different forms and should not be construed as limited to the embodiments set forth herein. Rather, these embodiments are provided so that this disclosure will be thorough and complete, and will fully convey the scope of the invention to those skilled in the art.

Embodiments of the invention provide modifications to known fluoroscopy filtering approaches that allow a cost effective mobile fluoroscopy system to be implemented using low cost single core and multi-core digital signal processor (DSP) integrated circuits (IC). Embodiments of the invention perform real time fluoroscopy image processing on low power DSPs by balancing loading of processing elements within the DSP cores and data movement in and out of the DSP cores. Aspects of the known filtering algorithms are modified to allow data sets used by the filter algorithm to be totally resident within high speed cache memory within the DSP cores in order to provide real-time processing rates.

Spatio-temporal filtering is one of the favored ways to process fluoroscopic image sequences. The approaches described herein are fairly representative of operations done in such algorithms. FIG. 1 shows Spatio-Temporal filtering approach 100 with object detection. A sequence of input images ($X_1, X_2, \ldots$) are enhanced using a matched filter or an unsharp masking operation 102 to create likelihood images $L_1, L_2, \ldots$ which are then spatially filtered 104 to form filtered images $S_1, S_2, \ldots$ and temporally filtered 106 to form output images $Y_1, Y_2, \ldots$. The spatial and temporal filtering operations are adapted using the likelihood images obtained in the image enhancement step. The unsharp masking approach could be used for a wide variety of applications, while the matched filtering approach is more complex but gives superior performance in presence of intervening medical objects like catheters of guide-wires. The matched filter and unsharp mask operations use single or multiple large sized (e.g. 13×13) kernels with fixed coefficient for the 2D convolutions while the spatial filter uses a small kernel (e.g. 3×3) with the filter coefficients adapted using local statistics obtained from the likelihood images. The temporal filter uses a first order IIR filter with the filter weight adjusted pixel-by-pixel, based on the likelihood images.

Figure 2:
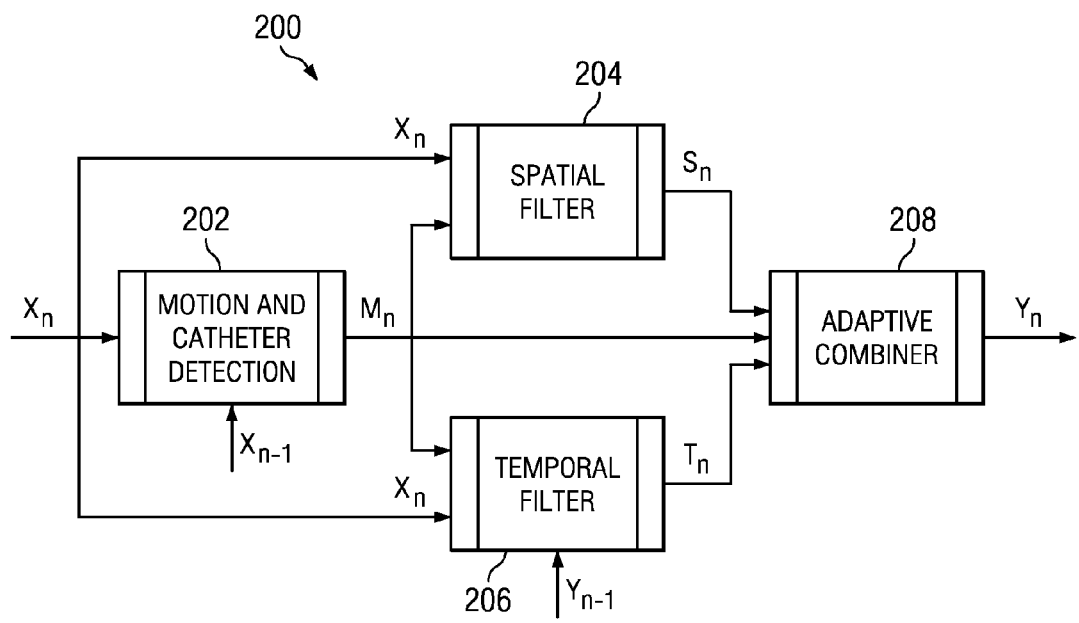

An approach 200 as shown in FIG. 2 uses a multi-step adaptive spatio-temporal filtering scheme, specifically tailored for applications like angiography. The first step involves generating a normalized motion mask 202 by normalizing the difference between two successive frames and then setting the catheter locations, which are detected as a moving line like structure, to unity. Next, each frame is processed using a spatial filter 204 which uses a rotated anisotropic kernel, guided by the motion mask generated in the motion detection 202 step. A temporal filter 206 processes the input image guided by the motion mask generated in motion detection step 202. Finally an IIR filter is used to combine 208 the spatially filtered image with the previous output image, where the motion mask is used to control the amount of spatial and temporal filtering.

The algorithms shown in FIGS. 1 and 2 were implemented in floating point, and used to process a fluoroscopic image sequence corrupted with Poisson noise, thereby simulating a low-exposure acquisition. The noise was added without changing the mean gray scale of the images.

The algorithm parameters (notation kept consistent with the references) chosen are as given below, Parameters Used with Approach 200
  2D Gaussian derivative kernel of size 11×11, with $\sigma=2$.
  For the backtracking step in detection line-like structures, $n=3$.
  Eigenvalue thresholds controlling backtracking operation are 1.3 and 1.1.
  Spatial filter using rotated anisotropic Gaussian kernel of size 7×7, with $\sigma_x = \sigma_y = 3$.
  First order IIR used for temporal filtering with weights allowed varying between 0.5 and 1.
Parameters Used with Approach 100 Using an Unsharp Mask Filter
  Conical model of unsharp mask filter with kernel size 13×13
  Spatial Filter of size 3×3 with $\gamma_{sp} = -0.3$, $\beta_{sp} = 50$
  First order IIR used for temporal filtering with $\gamma_{tmp} = 0.1$, $\beta_{tmp} = 250$, $k_{max} = 1$, $k_{min} = 0.5$.

Parameters Used with Approach 100 Using a Matched Filter
  Four matched filters with orientations: (0°, 45°, 90°, 135°)
  Cylindrical model of matched filter with kernel size 13×13 (catheter of size 9×3)
  Spatial Filter of size 3×3 with $\gamma_{sp} = -0.3$, $\beta_{sp} = 50$
  First order IIR used for temporal filtering with $\gamma_{tmp} = 0.1$, $\beta_{tmp} = 250$, $k_{max} = 1$, $k_{min} = 0.5$.

Figure 3B:
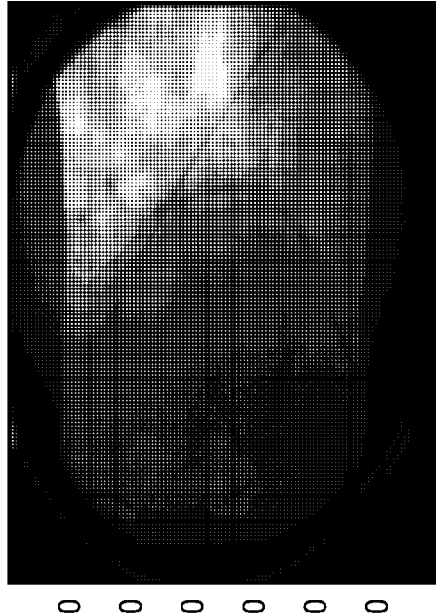
FIGS. 3A-3D are images illustrating performance comparison between approaches.
Figure 3D:
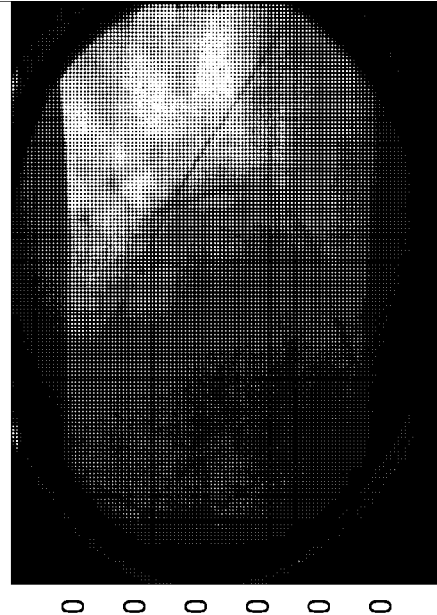
Figure 3A:
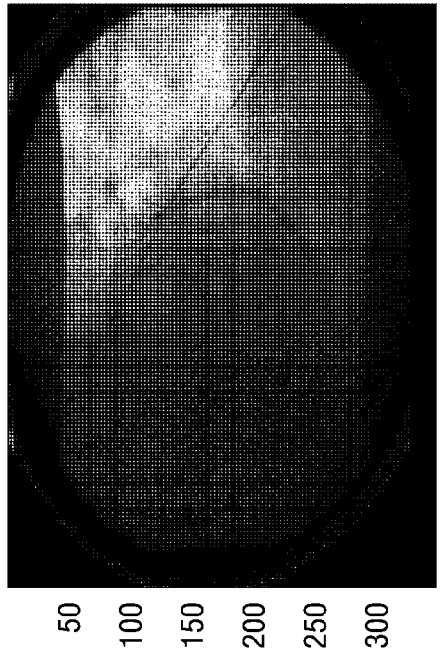
Figure 3C:
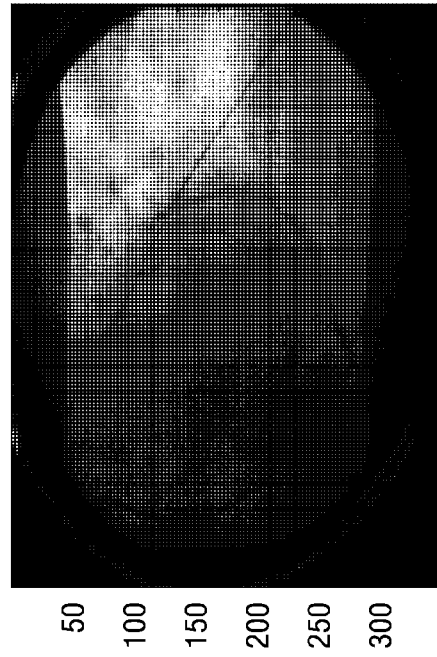

One of the noise corrupted frames, with $\lambda=0.25$, namely frame 13 from a sequence of 31 frames, is shown in FIG. 3A. FIGS. 3B-3D show its enhanced counterparts obtained by applying the algorithms described above. FIG. 3B shows frame 13 after being enhanced using approach 200. FIG. 3C shows frame 13 after being enhanced using approach 100 using matched filtering, while FIG. 3D shows frame 13 after being enhanced using approach 100 using unsharp masking.

Apart from evaluating these images visually, the image sequences were evaluated using a variety of objective image measures. The objective measures included the peak signal to noise ratio (PSNR) and overall image quality index obtained by comparing the outputs to the original images as regards luminance, contrast and structure preservation using a root mean squares approach. From Table 1, it can be seen that the apart from the PSNR and structure preservation indicator, the other objective measures, including the overall quality index, were very close among the various approaches.

TABLE 1

Functional performance comparison of various algorithms

| Approach | PSNR Improvement | Luminance improvement | Constrast improvement | Structure improvement | Overall quality index (Q) improvement |
|---|---|---|---|---|---|
| Using approach 200 | 9.43 | 0.97 => 0.90 | 0.42 => 0.82 | 0.33 => 0.55 | 0.25 => 0.38 |
| Using matched filter in approach 100 [0006] | 6.77 | 0.97 => 0.98 | 0.42 => 0.77 | 0.33 => 0.41 | 0.25 => 0.35 |
| Using unsharp masking in approach 100 | 6.55 | 0.97 => 0.98 | 0.42 => 0.81 | 0.33 => 0.43 | 0.25 => 0.37 |

It can be seen that at high levels of noise, as shown in FIG. 3A, approach 200 gave arguably better results, as shown in FIG. 3B. However, at lower levels of noise the difference between the approaches decreased. Moreover, it was observed that for a wide variety of test cases, the two versions of approach 100, matched filtering and unsharp masking, provide good performance at a significantly lower complexity than approach 200, making their performance-complexity tradeoff more attractive for real-time implementation. Hence these two variants were chosen for real-time implementation in one embodiment, as explained in the next sections. However, another embodiment may use algorithm 200 with modifications similar to those described below. Likewise, other known or later developed fluoroscopy filtering algorithms may be modified as described below for implementation on low cost DSP portable or stationary systems.

Architecture of a DSP Core

Figure 4:
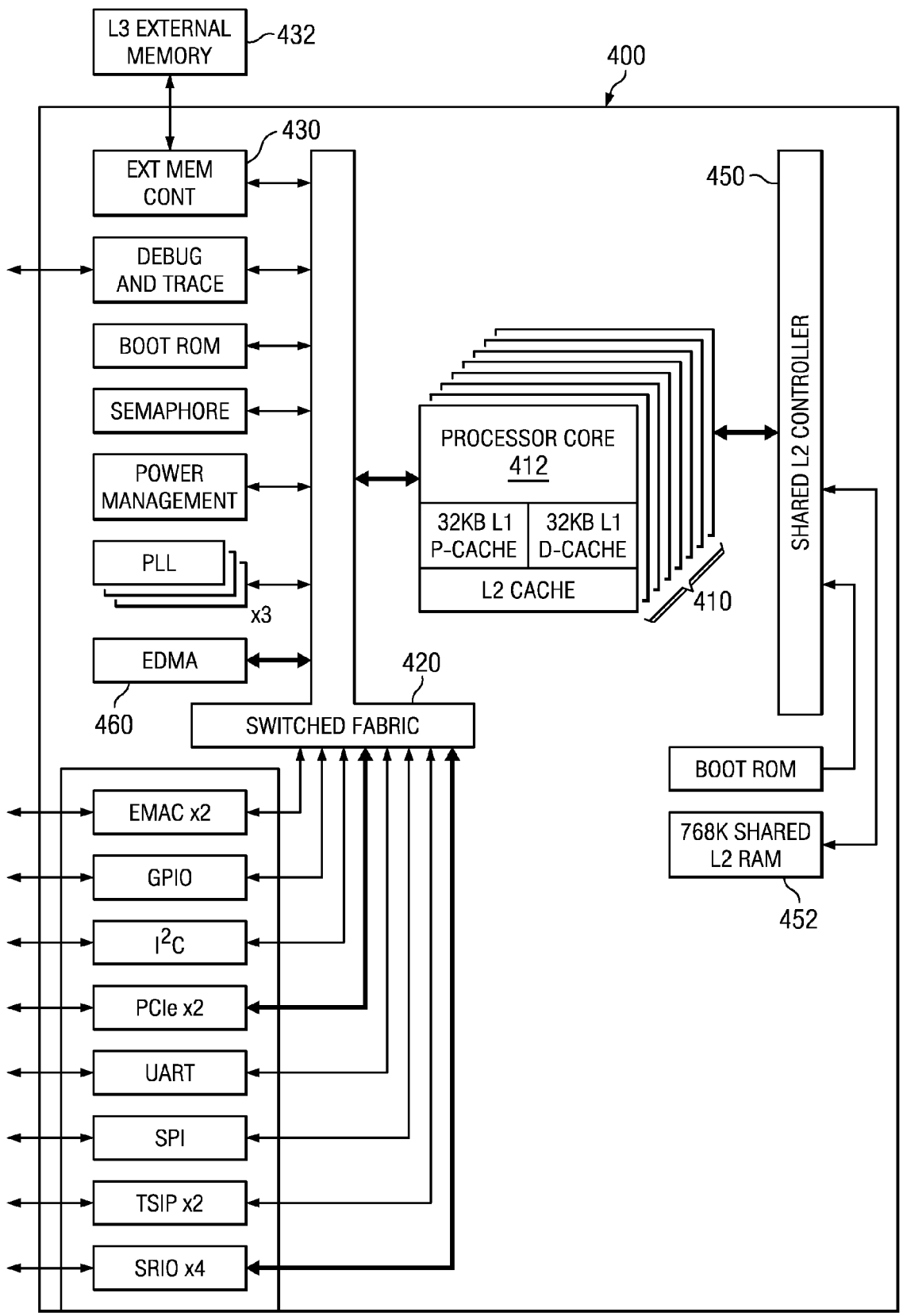
FIGS. 4-5 are block diagrams illustrating a DSP architecture.

FIG. 4, which is a functional block diagram of a system on chip (SoC) 400 that includes an embodiment of the invention. Before optimizing an algorithm for any architecture, it is important to understand its architecture. System 400 is a multi-core SoC that includes a set of processor modules 410 that each include a processor core 412, level one (L1) data and instruction caches, and a level two (L2) cache. In this embodiment, there are six processor modules 410; however other embodiments may have fewer or greater number of processor modules. In this embodiment, each processor core is a digital signal processor (DSP); however, in other embodiments other types of processor cores may be used. A switch fabric 420 provides high-speed interconnects with external memory controller 430 and external memory 432 to provide an extensive three-layer memory structure in which data flows freely and effectively between processor modules 410, as will be described in more detail below. An example of SoC 400 is embodied in an SoC from Texas Instruments, and is described in more detail in "TMS320C6472—Fixed-Point Digital Signal Processor Data Manual", SPRS612, July 2011, which is incorporated by reference herein.

There are three levels of memory in the SoC 400. Each processor module 410 has its own level-1 program (L1P) and level-1 data (L1D) memory. Additionally, each module 410 has a local level-2 unified memory (L2). Each of the local memories can be independently configured as memory-mapped SRAM (static random access memory), cache or a combination of the two. Data stored in the L1D memory and instructions stored in the LIP memory may be accessed in one execution cycle of the processor core. Thus, when accessing data in the L1D memory, no waits states are incurred and a maximum processing rate is possible. Accessing data stored in the L2 memory or in external memory may incur wait states.

In addition, SoC 400 includes shared L2 memory controller 450 and shared L2 memory 452. Shared external memory controller 430 and internal memory controller 450 allows processor modules 410 to dynamically share the internal and external memories for both program and data.

Processor modules 410, the enhanced direct memory access (EDMA) traffic controllers 460, and the various system peripherals can be classified into two categories: masters and slaves. Masters are capable of initiating read and write transfers in the system and do not rely on the EDMA for their data transfers. Slaves on the other hand rely on the EDMA to perform transfers to and from them. Examples of masters include the EDMA traffic controllers, serial rapid I/O (SRIO), and Ethernet media access controller (EMAC). Examples of slaves include the serial peripheral interface (SPI), universal asynchronous receiver/transmitter (UART), and inter-integrated circuit (I2C) interface.

Figure 5:
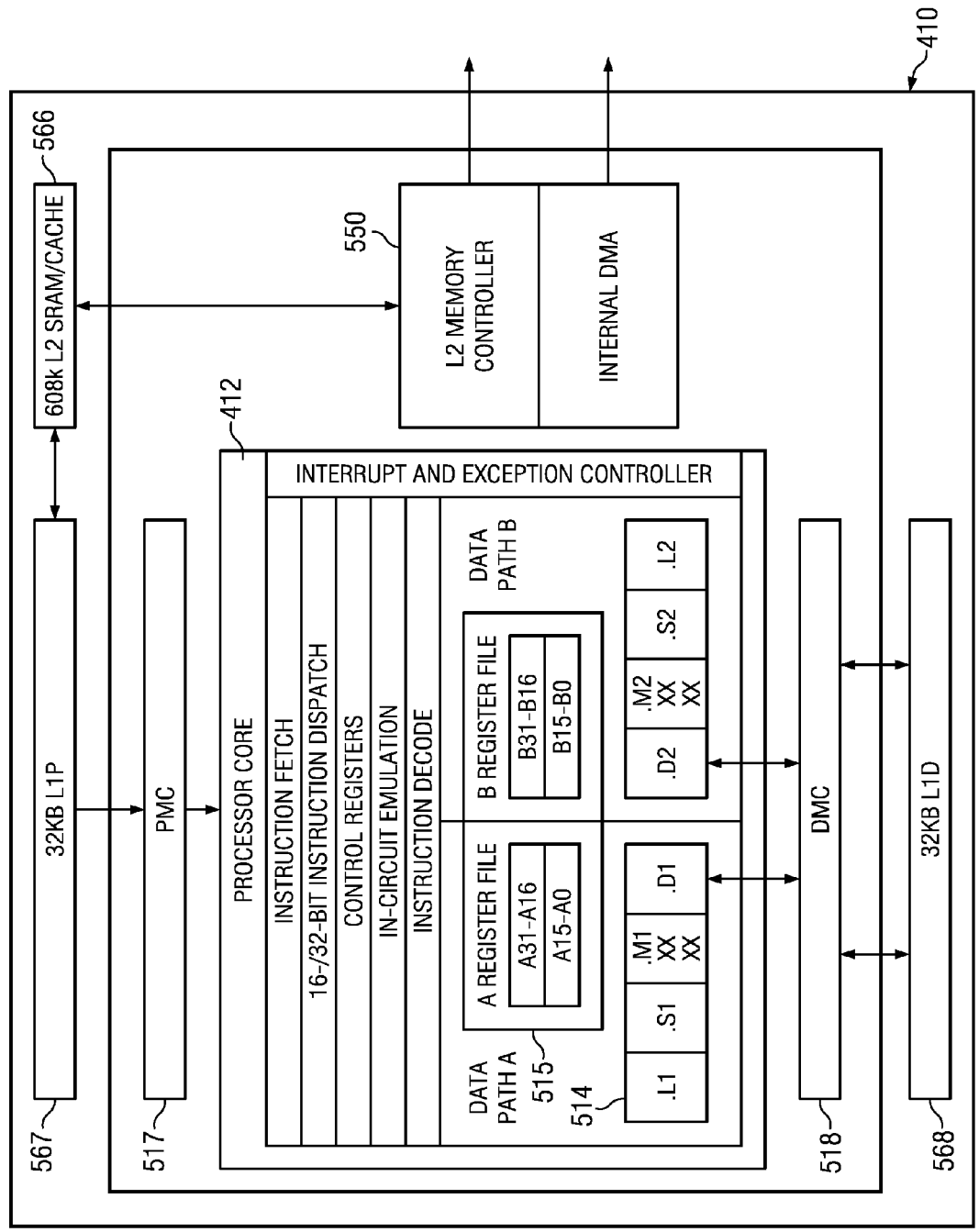

FIG. 5 is a more detailed block diagram of one processing module 410 used in the SoC of FIG. 4. DSP processor core 412 includes eight functional units 514, two register files 515, and two data paths. The two general-purpose register files 515 (A and B) each contain 32 32-bit registers for a total of 64 registers. The general-purpose registers can be used for data or can be data address pointers. The data types supported include packed 8-bit data, packed 16-bit data, 32-bit data, 40-bit data, and 64-bit data. Multiplies also support 128-bit data. 40-bit-long or 64-bit-long values are stored in register pairs, with the 32 LSBs of data placed in an even register and the remaining 8 or 32 MSBs in the next upper register (which is always an odd-numbered register). 128-bit data values are stored in register quadruplets, with the 32 LSBs of data placed in a register that is a multiple of 4 and the remaining 96 MSBs in the next 3 upper registers.

The eight functional units (.M1, .L1, .D1, .S1, .M2, .L2, .D2, and .S2) are each capable of executing one instruction every clock cycle. The .M functional units perform all multiply operations. The .S and .L units perform a general set of arithmetic, logical, and branch functions. The .D units primarily load data from memory to the register file and store results from the register file into memory. Each .M unit can perform one of the following fixed-point operations each clock cycle: one 32×32 bit multiply, two 16×16 bit multiplies, two 16×32 bit multiplies, four 8×8 bit multiplies, four 8×8 bit multiplies with add operations, and four 16×16 multiplies with add/subtract capabilities. Many communications algorithms such as FFTs and modems require complex multiplication. The complex-multiply (CMPY) instruction takes four 16-bit inputs and produces a 32-bit real and a 32-bit imaginary output. There are also complex multiplies with rounding capability that produce one 32-bit packed output that contains 16-bit real and 16-bit imaginary values. The 32×32 bit multiply instructions provide the extended precision necessary for audio and other high-precision algorithms on a variety of signed and unsigned 32-bit data types.

Each processor module 410 in this embodiment contains a 608 KB level-2 memory (L2) 566, a 32 KB level-1 program memory (L1P) 567, and a 32 KB level-1 data memory (L1D) 568. The device also contains a 768 KB multi-core shared memory 452. All memory in SoC 100 has a unique location in the memory map The L1P and L1D cache can be reconfigured via software through the L1PMODE field of the L1P Configuration Register (L1PCFG) and the L1DMODE field of the L1D Configuration Register (L1DCFG) of each processor module 410 to be all SRAM, all cache memory, or various combinations. L1D is a two-way set-associative cache, while L1P is a direct-mapped cache.

L2 memory can be configured as all SRAM, all 4-way set-associative cache, or a mix of the two. The amount of L2 memory that is configured as cache is controlled through the L2MODE field of the L2 Configuration Register (L2CFG) of each processor module 410.

Global addresses are accessible to all masters in the system. In addition, local memory can be accessed directly by the associated processor through aliased addresses, where the eight MSBs are masked to zero. The aliasing is handled within each processor module 410 and allows for common code to be run unmodified on multiple cores. For example, address location 0x10800000 is the global base address for processor module 0's L2 memory. DSP Core 0 can access this location by either using 0x10800000 or 0x00800000. Any other master in SoC 100 must use 0x10800000 only. Conversely, 0x00800000 can by used by any of the cores as their own L2 base addresses.

Level 1 program (L1P) memory controller (PMC) 517 controls program cache memory 567 and includes memory protection and bandwidth management. Level 1 data (L1D) memory controller (DMC) 518 controls data cache memory 568 and includes memory protection and bandwidth management. Level 2 (L2) memory controller 550 includes memory protection and bandwidth management and controls internal L2 memory/cache 566 and is coupled to shared L2 memory controller 450 for access to shared L2 memory 452.

During every clock cycle, the instruction fetch, dispatch, and decode units deliver instructions to the eight functional units that reside in the two data paths (A and B) as shown in FIG. 5. Each data path contains four functional units (L, S, M, and D) and 32 general-purpose registers and every unit may produce a result at each clock cycle when the operations are balanced. Data stored in the L1D memory may be accessed in one execution cycle of the processor core. Thus, when accessing data in the L1D memory, no waits states are incurred and a maximum processing rate is possible. Accessing data stored in the L2 memory or in external L3 memory may incur wait states.

The complexity of the fluoroscopy filtering algorithm is approximately the complexity of the loop kernels which dominate the complexity of these algorithms. In addition to the complexity of the loop kernel, every loop typically has loop setup and wind-down instructions (epilog and prolog). In the presence of nested loops, only the innermost loop gets pipelined by the compiler, and the overheads of the inner loops get multiplied by the number of times the outer loops are executed. Hence where possible, the largest loops are made the innermost loops. In addition to loop overheads, certain operations may occur only in the outer loops, and hence do not get pipelined. Such operations may be minimized and if necessary the loops are split by using temporary storage. To achieve lowest complexity, the implementation may need to change the algorithm data path in ways the do not affect performance of the filter algorithm. This may involve known techniques for optimizing code, such as loop unwinding, hand tuning of code segments to balance functional unit loading, etc.

DSP Implementation of Real-Time Fluoroscopy Image Processing

After simulating the floating point MATLAB performance of these algorithms to produce the results illustrated in FIGS. 3A-3D, each of them were converted to fixed point DSP implementations. In an embodiment of the invention, a DSP implementation uses several structures and functions which are optimized for execution speed on the DSP cores described above. All the modules accept 16-bit input data, and use 16-bit internal precision. The output of the matched filter and unsharp mask is saturated to user defined levels (set to +/−512), while the output of the spatial and temporal filters are also saturated to user defined levels (set to 255).

Optimization details of the various algorithms will now be described in more detail. The matched filter implementation uses four user-defined filters, each of size 13×14 and using signed 16-bit coefficients. Each row of the filter is extended to 14 elements (from the 13×13 kernel used for all evaluations) to facilitate efficient wide load DSP operations. The last element of each row is set to zero, to keep the effective filters of size 13×13. Although for evaluation purposes the filters were obtained by rotating the basic kernel, the implementation did not try to take advantage of this and would give the same cycle-performance even if they were completely different. The image edge pixels are set to user defined values. For each output point, four 2D filtering operations needs to be done, and the maximum value chosen. Two implementation variants were evaluated. The first approach used a two step procedure in which each of the filtered outputs was stored into an intermediate scratch memory during the first step, while the second step looped through all the intermediate stored values pixel-by-pixel, calculated the maximum, and generated the outputs. This approach used extra scratch memory, suffered from the overhead of additional loads and stores of the intermediate data, but benefited from the fact that both the steps could use pipelined loops. The second approach did not use in temporary storage, and instead computed the four matched filter values in the innermost kernel, and then did the maximization and storage within the outer loop. Although this approach did not benefit from pipelining the operations done in the outer loop, it used less memory and was found to be the more efficient one in actual implementation. Also the innermost kernel for this approach was multiply-limited and achieved parallelization of eight multiplies per cycle—the maximum possible for this architecture.

Instead of matched filtering, the image could be enhanced using unsharp masking. The unsharp masking operation involves two dimensional filtering with a large kernel sized fixed filter. Similar to the matched filter, this implementation uses 13×14 sized filters, in which typically only 13×13 values are non-zero. The edge pixels are handled similar to the matched filter algorithm. Here again, the innermost loop over the mask columns is completely unrolled and results in a 3-level nested loop, which is register and logic unit limited.

The spatio-temporal filter supports three modes of filtering—spatial, temporal and spatio-temporal filtering. The spatial filter uses a 3×3 adaptive filter kernel with the coefficients generated from a look-up-table (LUT) implementing $1/(1+\exp(z))$, where z is a scaled argument that will be described in more detail below. Experimentally it was determined that a 1 KB LUT was sufficient to provide the desired functional performance. For every pixel (x,y) in a 3×3 neighborhood of the center pixel $(x_c,y_c)$, the argument, z, to this LUT was a scaled version of the difference $(L(x,y)-L(x_c,y_c))$, where L is the likelihood image generated in the previous step. The Q-points of the LUT argument and scale coefficients ($\gamma$, $\beta$) are synchronized for efficiency. The final normalization step for computing the output value involves a fixed point division operation, and is carried out in a separate loop to facilitate pipelining. Again the innermost loop over the mask columns is completely unrolled and results in a 3-level nested loop. The temporal filter implements a first order IIR filter and does a pixel-by-pixel weighted combining of the current spatial filter output and the previous temporal filter output. In the absence of a spatial filter, the temporal filter could work directly on the input image. The weights are scaled outputs of the same LUT as the spatial filter, and the LUT arguments are scaled pixel-by-pixel differences between the current and previous likelihood images. The spatio-temporal filter is functionally equivalent to spatial filtering followed by temporal filtering, but has a different sequencing of operations. It generates a single spatially filtered row, and then uses it to generate a temporally filtered row-m before going back to generate the next spatially filtered row. This approach bypasses the need for separate spatially filtered outputs.

Table 2 provides a summary of the performance of the algorithms on a C64x+ cycle accurate simulator, assuming a flat memory model. In other words, no data movement and cache effects were considered. The second column of the table gives the number of nested loops in the implementation. Typically, a higher number of nested loops results in more loop overhead. In all the algorithms, at least one of loops is completely unrolled to minimize overheads and maximize the register usage while maintaining optimum unit loading. The type of unit (L, M, S, D) which limits the performance of the algorithm is given in the third column, while the overall cycle performance is given in the fourth column.

TABLE 2

Performance of algorithms on C64+ cycle accurate simulator (flat memory model)

| Algorithm | Number of nested loops | Limiting resource | Cycles per Pixel |
|---|---|---|---|
| Matched Filter (MF) | 4 | M, Registers | 135 |
| Unsharp Masking (UM) | 3 | LSD, Registers | 55 |
| Spatio-temporal Filter (STF) | 3 | D | 33 |

LUT Simplification for Spatial and Temporal Filtering

Figure 6:
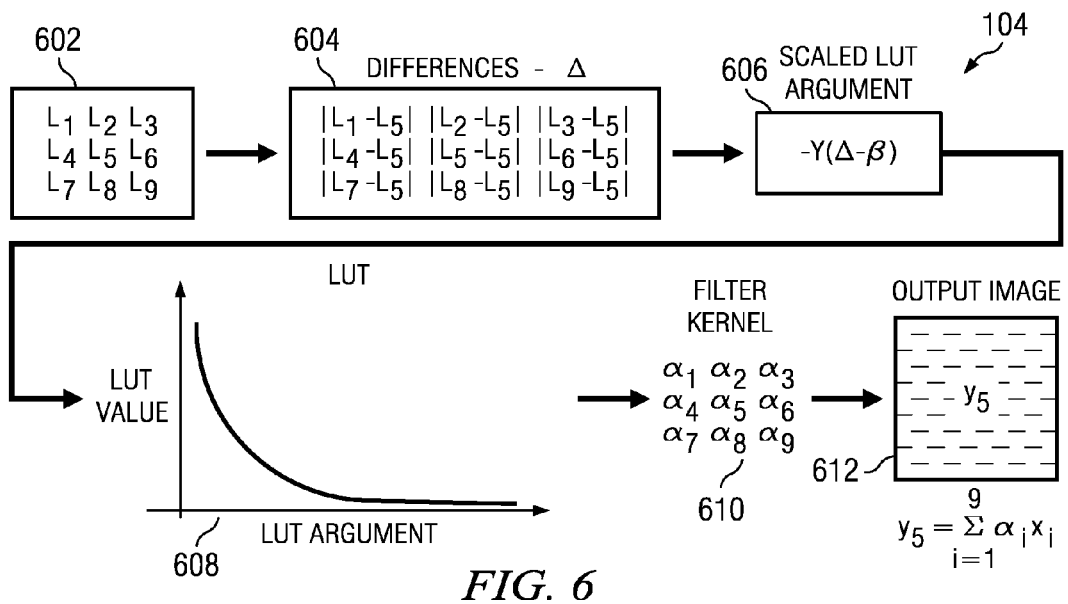
FIG. 6 is a flow diagram illustrating operation of a modified spatial filter.

FIG. 6 illustrates operation of a modified spatial filter 104 in more detail. Adaptive spatial processing is done with a (2n+1)×(2m+1) kernel. In this embodiment, a nine element kernel 602 is used.

In general, the α's are obtained from a look-up-table (LUT), according to equation (1).

$$\alpha_{i,j} = LUT(|L(x_0,y_0) - L(x_i,y_j)|, \gamma_{sp}, \beta_{sp}), \quad (1)$$

for i=−n, . . . , n and j=−m, . . . , m
where $L(x_i, y_i)$ are pixel values from the object-likelihood image as output by the matched filter or unsharp filter 102, referring back to FIG. 1 and $\gamma_{sp}$ and $\beta_{sp}$ are parameters which define the spatial filter LUT function. The method is arranged to not filter across object boundaries, and the pixel weights, the α's, depend upon the absolute difference between center and surround object likelihood pixels. When the absolute difference is large, a boundary is present, and those pixels across the boundary are not heavily weighted.

Previously, the LUT used the formula in equation (2).

$$LUT(\Delta, \gamma, \beta) = \frac{1}{1 + \exp(-\gamma(\Delta - \beta))} \quad (2)$$

where Δ refers to the difference in pixel intensity in the likelihood image as defined in equation (1), γ specifies a gradient and β specifies the horizontal shift.

A direct implementation of this LUT, even for a given γ and β can be quite large. For example, using 32 bit values, and 16 bit pixel intensity values (value of x), the LUT would need to store 65,536 32-bit numbers, taking a total of 256 Kbytes.

Moreover, previously, a separate LUT was required for the temporal filtering step of processing. In the temporal filter, the estimate of a pixel intensity $\hat{I}_t(x, y)$, at coordinates (x, y) and time t, is given by equation (3).

$$\hat{I}_t(x,y) = \hat{I}_{t-1}(x,y) + \kappa[I_t(x,y) - \hat{I}_{t-1}(x,y)] \quad (3)$$

where $I_t$ is the measured intensity at the current time instant, and κ is a filter gain which depends upon space and time. The filter is applied independently to each pixel, $I_t(x, y)$ in the image. The amount of temporal filtering is controlled using the object likelihood images. A control image is obtained by subtracting the present image, $L_t$, from the last one, $L_{t-1}$. The value for κ comes from a LUT operation applied at each pixel location (x, y), as shown in equation (4).

$$\kappa = LUT(|L_t - L_{t-1}|, \gamma_{tmp}, \beta_{tmp}) \cdot (\kappa_{max} - \kappa_{min}) + \kappa_{min} \quad (4)$$

where $L_t$ is the likelihood value (output of matched filtering/unsharp masking stage 102 of processing) of the corresponding pixel for frame t; $\gamma_{tmp}$ and $\beta_{tmp}$ are temporal filter LUT parameters in a logistic sigmoid function, and $\kappa_{min}$ and $\kappa_{max}$ are limits of κ. Since the absolute value $|L_t - L_{t-1}|$ is used, a large value of the argument indicates the presence of an object in the current or previous frames, but not both. In this case, reduced filtering is desired, and an upper limit $\kappa_{max}$ of less than or equal to one is used. When the LUT argument is small, either there is no object present, or an object is present in both frames, and a small value $\kappa_{min}$ greater than or equal to 0 is desired.

A implementation of this LUT using parameters discussed for the spatial filter LUT would need an additional 256 Kbytes of storage.

These two massive LUTs would not fit within the L1 data cache of the DSP cores described above and performance would thereby be reduced due to cache thrashing and/or wait states incurred while accessing L2 or L3 memory levels. Therefore, in this embodiment, the spatial filter LUT is modified to be a LUT that contains 1024 16-bit values of LUT(Δ)=1/1+exp(z), where z is linearly spaced in the range −8 to 8. For each access into the LUT, the precision of z is truncated to match the precision of the LUT. If the value of z exceeds 8 or −8, then the LUT entry for 8 or −8, respectively, is used. This is possible by simply scaling the LUT argument z on the fly, according to equation (5). This allows the entire LUT to be maintained in level 1 memory that can be accessed by the processor core without incurring a wait state.

$$z = -\gamma(\Delta - \beta) \quad (5)$$

where Δ is the difference in each pair of likelihood pixels according to equation (1) for the spatial filter and according to equation (4) for the temporal filter.

Note that the spatial function uses:

$$Z\_1 = -\gamma\_sp * (|L(x,y) - L(x\_i, y\_j)| - \beta\_sp) \quad (6)$$

where L(x,y) is the pixel value of the current likelihood image at coordinate (x,y); and L(x_i,y_j) are the likelihood values in the 3×3 neighborhood of (x,y).

Whereas the temporal filter uses:

$$Z\_2 = -\gamma\_tmp * (|L\_t(x,y) - L\_\{t-1\}(x,y)| - \beta\_tmp) \quad (7)$$

where $L\_t(x,y)$ and $L\_\{t-1\}(x,y)$ are the pixel values of the current and previous likelihood images at coordinate (x,y).

Thus for a given (x,y) coordinate, the spatial filter and the temporal filter will look up different values from the likelihood images, followed by different mappings to produce different Z_1 and Z_2; which will be then used to access the same LUT.

Referring again to FIG. 6, in this modified spatial filter, for each pixel in the input image frame, differences D between a center pixel and the surrounding eight pixels in the associated likelihood image are determined 604. Each difference value D is then scaled 606 to produce a value z. The z value is then used as an argument to access the spatial filter LUT 608 to produce the $\alpha_i$ value kernel 610 which is then used to compute 612 the spatially filtered output image pixel.

In a similar manner by adjusting the temporal filter LUT argument on the fly, this same table may be used for the spatial and the temporal filtering for different values of γ and β. Therefore a two Kbytes table is sufficient to achieve the desired performance and easily fits into the 32 KByte L1 data cache memory available on the DSP core. This single LUT works even if the filter parameters are changed real-time since the new values would then be used for the on the fly argument adjustments. In fact, further savings in data memory could be achieved by spreading out these LUT argument values non-uniformly. For example, the smaller (absolute) values of z may be closely spaced, and the larger value spaced further apart.

Mapping to Single C64x+ Core

Figure 7:
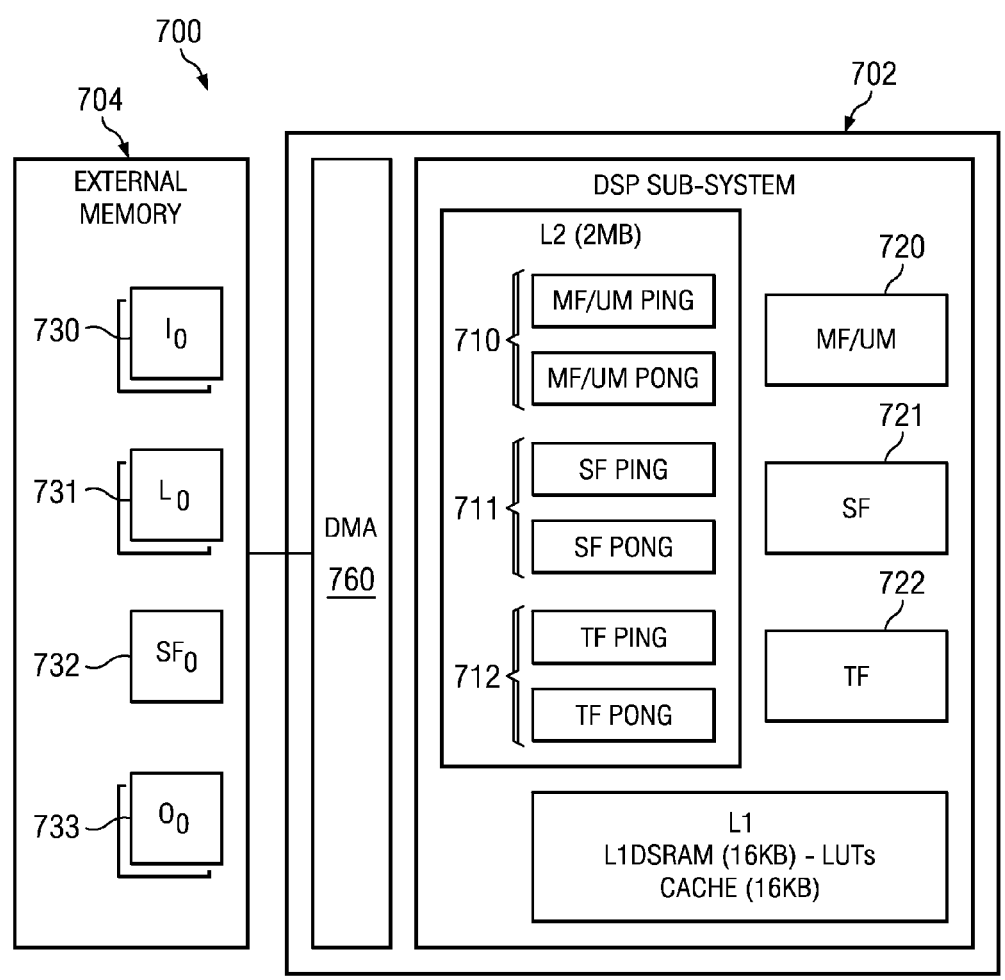
FIG. 7 shows overall memory usage of fluoroscopy system in the DSP architecture of FIG. 5.

A scheme for mapping these optimized algorithms to the memory architecture of the DSP core(s) described previously with regard to FIGS. 4-5 will now be described in more detail. In this example, a single core TMS320C6455 device 702 is used with an external memory 704. This single core device is available in various flavors with clock rates up to 1.2 GHz, 32 KB L1 program and data RAM, 2 MB L2 RAM and can deliver performance up to 9.6 GMACs (multiply and accumulate per second). A typical implementation, consisting of modules for matched filter (MF) or unsharp masking (UM), followed by spatial filtering (SF) and temporal filtering (TF), on such a device is shown in FIG. 7.

To get optimum performance, the L1 data memory is partitioned equally into cache and non-cache, while the entire L1 program memory is kept as cache. All the filter code 720-722 is loaded into the L2 RAM, which in this device is 2 MB. During operation, the L1 cache controller automatically pulls each module 720-722 into L1 program cache when required. The data is kept in non-cache L1 data memory, included all the matched filter and unsharp mask coefficients, the 2 KB LUT used by the spatio-temporal filter, and the frequently used data structures and parameters. The large data sets, namely all the input data frames 720, the most recent two likelihood images 721 (current and previous frames of output from the image emphasis step) and all the output data frames 722, 723, are too large to be kept in the L2 memory, and therefore are stored in the 256 MB of external DDR memory 704.

These image data sets are transferred from external memory onto the device's L2 memory, section-by-section, using the on-chip DMA controller 760 and a double buffering scheme, and from there are automatically pulled into the L1 cache, as and when required, by the device L1 data cache controller. Given the nature of the processing (2D filtering), which required access to data from previous and next rows to generate the current output, the sections are overlapped to the extent of the filter size. At each step, the algorithms consume $V=[Q+(L-1)]$ rows and generate Q rows (Q is chosen as 20) of output, where L is the length of the 2D filter used in that algorithm (matched filter/unsharp mask uses $L=13$, spatial filter uses $L=3$, temporal filter uses $L=1$). Hence several input and output buffers 710-712, each of size 2V and 2Q rows respectively, are created in the L2 memory. Note that the buffers are doubled in size to accommodate double ping-pong buffering. As the DMA can transfer data without CPU supervision, the double buffering scheme allows it to transfer one section of the image while the CPU is working on another section. This allows processing to proceed with minimal data transfer overhead.

Figure 8:
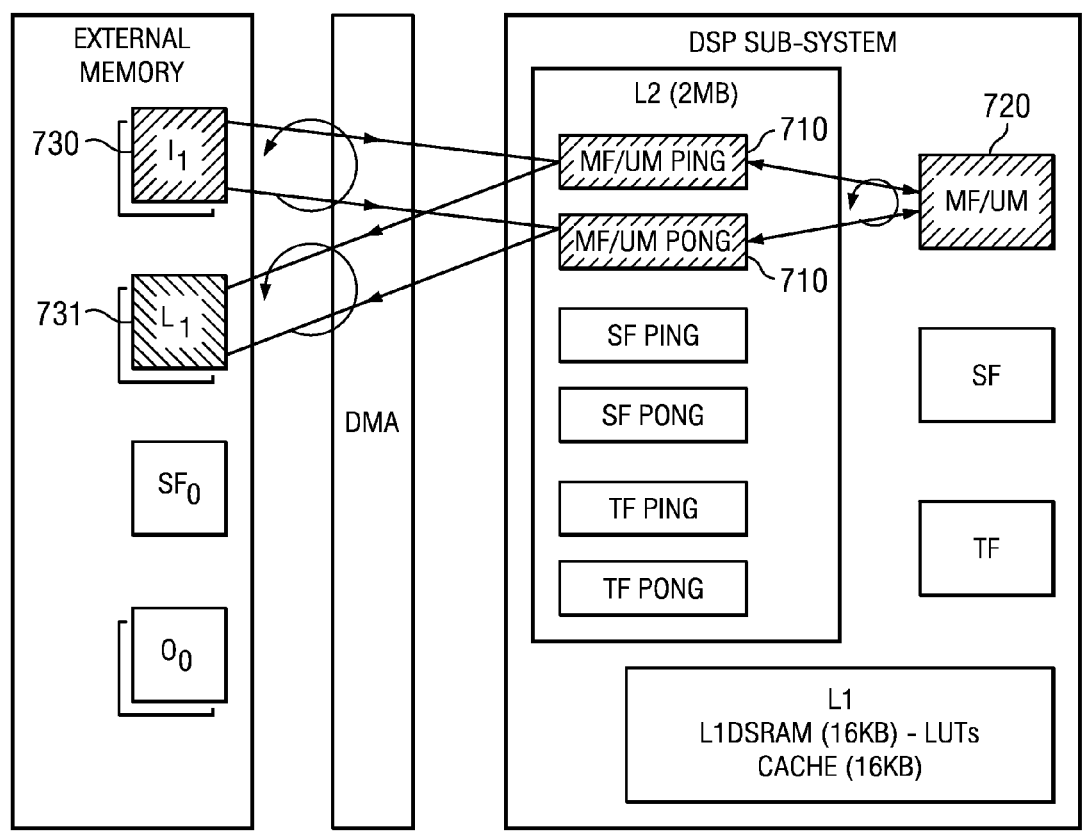
FIGS. 8-10 illustrate progress of data through various processing steps.
Figure 9:
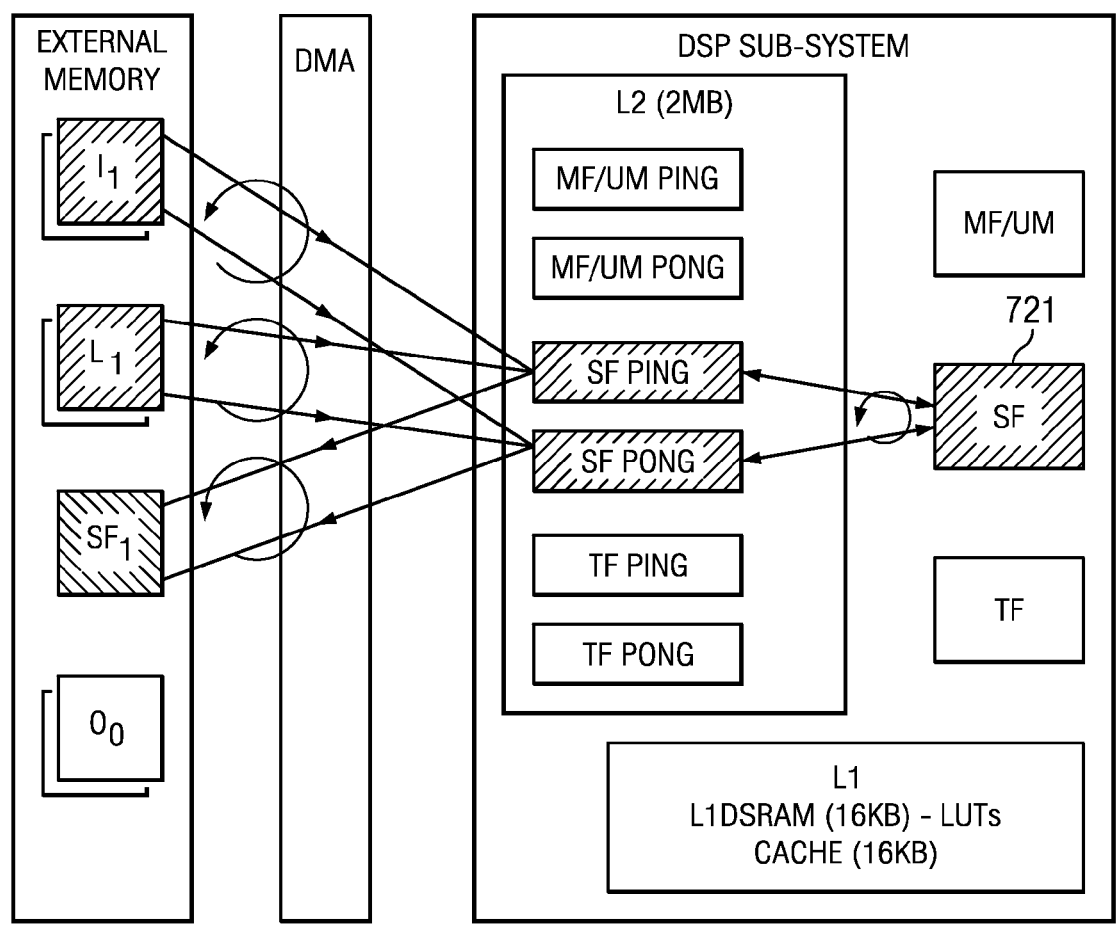
Figure 10:
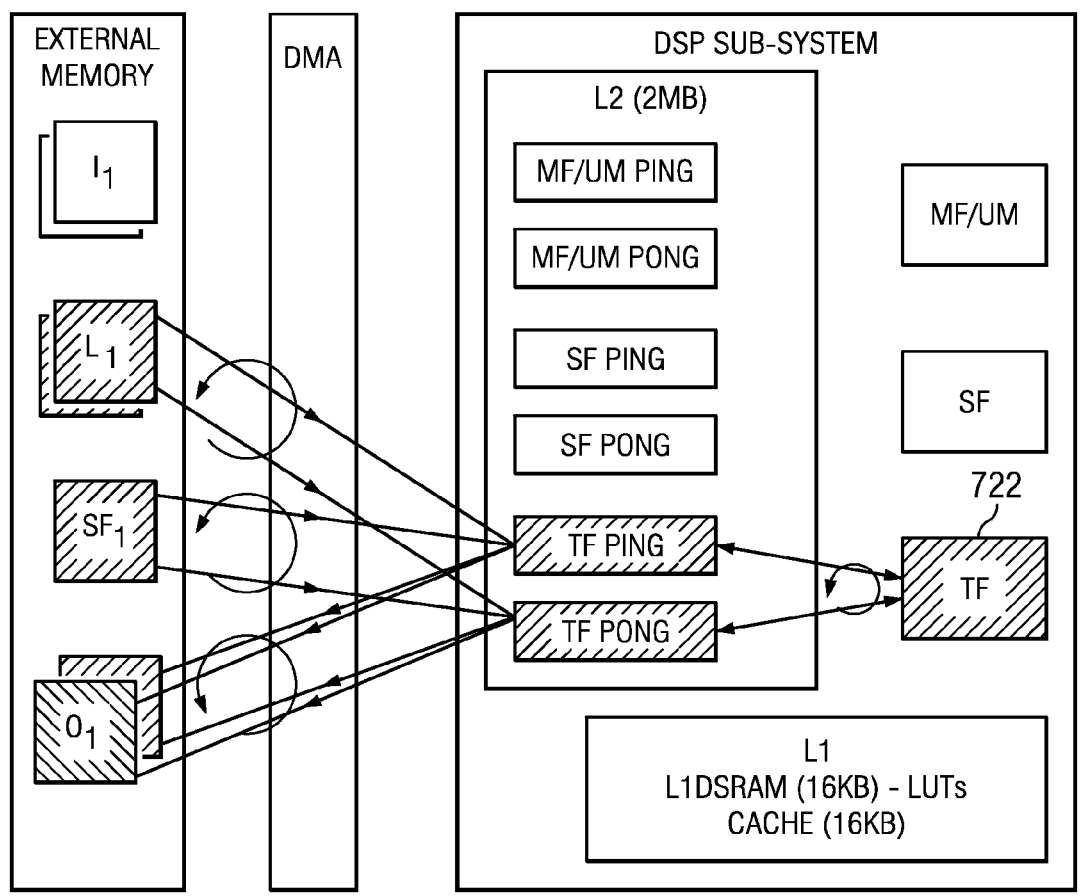

FIGS. 8-10 illustrate the progress of data through the various steps of processing. Before progressing further, the double buffering (or ping-pong buffering) scheme is explained. In a simplistic scheme, the DMA and processing would proceed sequentially. In other words, the DMAs would transfer the data from external memory to L2 buffers which would then be processed by the module to create L2 output buffers, which would in turn be transferred to external memory by the DMAs. This would lead to memory transfer overheads since the processing would need to wait till the data transfers are complete. In double buffering (ping-pong) schemes, the DMA transfers data from external memory to a set of input buffers in L2 memory (input ping buffers) and then transfers a set of output buffers (output ping buffers), processed by the module during the previous iteration, from L2 to external memory.

During this time, the module works on the input L2 buffers filled by the DMA during the previous iteration (pong input buffers) and generating outputs to the pong output buffers. After the module completes processing the pong buffers, it switches and starts processing the ping buffers (assuming that the DMAs are complete) and the DMAs start processing the pong buffers. This scheme ensures that if the processing is dominated by the processing complexity and not the DMA transfers, the data movement overhead is negligible. Of course, before the DMA and processing can start operating in tandem, the ping and pong buffers need to be filled a-priori (primed).

FIG. 8 illustrates the use of such a ping-pong scheme to enhance 720 an input image, $I_1$, and create likelihood image $L_1$. Next FIG. 9 shows that images $I_1$ and $L_1$ are used by the spatial filter 721 to create output $SF_1$, while FIG. 10 shows how the temporal filter 722 uses current and previous likelihood images ($L_1$ and $L_0$), the current spatially filtered image $SF_1$ and the previous output image $O_0$ to create the current output image $O_1$. As explained earlier, a more efficient implementation would collapse the spatial and temporal filtering, into a spatio-temporal filtering step and reduce DMA overheads.

Such an implementation on a single core device like the TMS320C6455 device produces results as given in Table 3, which compares the results of a cycle accurate simulator with a flat memory model versus the actual performance of the C6455 core. It can be seen that for computation-heavy modules, like the MF and UM modules, the cache penalty and data movement overhead combined to be in the range of 5% to 10%. In contrast, the data access and data movement heavy algorithm, namely the spatio-temporal filter (STF), has a penalty of ~50%. The heavy D unit usage (the kernel accesses several data arrays to create the output array) results in large cache penalties. Moreover despite using the double buffering scheme, both the cache controller and the DMA engine need to constantly access the L2 memory which causes contention and increases overhead.

TABLE 3

Performance of algorithms on C64+ cycle accurate simulator (flat memory model) versus performance on C6455 core

| Algorithm | Cycles per Pixel on Simulator | Cycles per Pixel on C6455 | Overhead |
| --- | --- | --- | --- |
| Matched Filter (MF) | 135 | 149 | ~10% |
| Unsharp Masking (UM) | 55 | 58 | ~5% |
| Spatio-temporal Filter (STF) | 33 | 46 | ~46% |

Mapping to Multi-Core Architectures

Multi-core devices from TI vary in the number and kind of processor cores, memory, connectivity and other peripherals. In this example, operation of the modified fluoroscopy filtering algorithm on a multi-core TMS320C6472 will be described. As was described with regard to FIGS. 4-5, this chip has six C64x+ megamodules with each megamodule consisting of a C64x+ fixed point DSP core, 32 KB of L1 program, 32 KB of L1 data RAM and 608 KB of local L2 RAM. The six megamodules share 768 KB of additional memory, DMA controller and several other peripherals. Each of the C64x+ cores support clock rates up to 700 MHz, yielding a maximum of 33.6 GMACs per SoC device.

In one embodiment, the memory arrangement remains similar to the single-core case. As before the large data sets are stored in the external memory, and the frequently used data sections are kept in the non-cache portion of the L1 memory for each the cores, i.e. multiple copies of the data are kept—one for each core. Similarly the ping-pong buffers are created (but made half the size of the single core case, since the L2 memory per core is smaller) in the L2 memory of each of the cores.

The processing is set up by a main control ("boss") thread running on the one of the cores, and the processing ("worker") threads running the remaining five cores. All the DMA operations are controlled by the boss thread, which directs the DMA to fill and empty the ping-pong buffers in the L2 memories of the cores running the worker threads. The worker threads process the input ping or pong L2 buffers, as instructed by the boss thread, and update the appropriate output buffers. The inter-thread communication, using message queues, is achieved using the IPC (inter-process communication) module available in SYS/BIOS. Messages are sent from the boss to each of the worker threads to process the ping (or pong) set of input buffers, while it instructs the DMA to process the pong (or ping) buffers. As soon as the worker processes the buffer, it sends a reply message to the boss, which in turn instructs it to process another set of buffers (assuming that the DMAs have completed by that time). As in the single core case, the L2 ping-pong buffers, for each of the cores, are primed at the start of processing.

System Level Memory Optimization

Typically in DSP systems, the large input/output images are stored in external memory, and DMA brings an image section from external memory to the ping buffer in L2 memory, while the CPU works on the previous (pong) buffer in L2 memory. Since the DMA and CPU work independently, maximum efficiency can be achieved as long as the CPU finishes processing the "pong" buffer, before the DMA finishes writing the "ping"-input buffer, and reading the "ping" output buffer. Now for 2D filtering with L×L kernels (odd L), using such ping-pong buffer schemes, the CPU would need to read O+L−1 rows, to produce O output rows. Reading these (L−1) edge rows twice for each section is the overhead associated with this scheme.

This overhead may be reduced by retaining the (L−1) previous rows in cache/L2 memory, and only bringing in the new "O" rows into L2 memory, thereby reducing the load on the DMA subsystem. This trick can help in single-core and multi-core systems.

Figure 11:
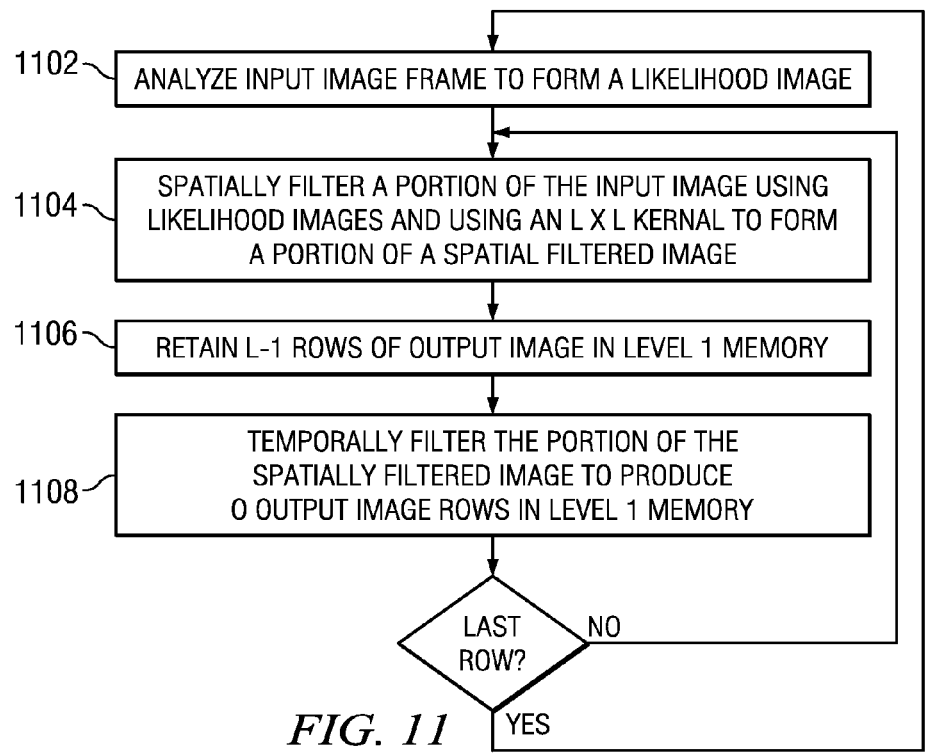
FIG. 11 is a flow diagram illustrating optimization of memory usage.

FIG. 11 is a flow diagram illustrating optimization of memory usage using the trick just described. In single core systems, the overall system was found to be efficient (less than 5%-10% overhead) for computation heavy algorithms like the matched filter and the unsharp masking 1102. However for the data-movement heavy algorithms, such as the spatial and temporal filtering the overhead can be very high. This is because the spatial filter needs the input I(1) and likelihood L(1) images to create the spatially filtered output SF(1) while the temporal filter needs the current spatially filtered images SF(1), the previous output image O(0), along with the likelihood images L(0) and L(1) to create the current output image O(1). Doing it in such a direct fashion—that is spatial filtering followed by temporal filtering, would cause the overheads to go up as high as 300%, especially for the temporal filtering step. This was found to be mainly due to L2 memory conflicts since both the DMA and the CPU need to access this memory at the same time. An alternate way to do this involves loading sections of I(1), L(1) and O(0) into L2 memory buffers—producing a small number of spatial filter outputs 1104, for example making SF(1) a single row wide (which can remain in L1 memory), and then consuming 1108 it right away to produce a single row of O(1). Such an approach uses the cache more efficiently, eliminates the need to access L2 memory for SF(1), and eliminates the need for the DMA to load the L(1) sections twice, once for spatial filtering and once for temporal filtering, since L−1 rows are retained 1106 in the L1 level memory. Due to all these changes the overhead came down to ~16% for the matched filter+spatio-temporal filter based system, and ~18% for the unsharp masking based system.

For and embodiment on a multicore device such as a TMSC6472 device, with six C64x+ megamodules that each have their own L1 and L2 memory, the L2 memory conflicts become less of an issue, simply because the L2 memories are independent. However the single DMA controller feeding all the L2 memories means that its bandwidth becomes the processing bottleneck. To overcome this roadblock, the processing is changed to do all steps for matched filtering/unsharp masking and spatio-temporal filtering on a small section of the image, before starting on the next image section. This bypasses the need to load to input data twice (once for MF/UM processing and once for STF processing), load the current likelihood image (since it was produced in the previous processing step, and immediately consumed) and the spatial filtered output. The input, previous output and previous likelihood images continued to be transferred in by DMAs and the final output and likelihood images continued to be transferred out. Thus, to produce M output rows for output image O(1) (assuming matched filtering based system), M rows of O(0) would be needed along with (M+LMF+LSF−2) rows of the input image. These rows would first be consumed by the matched filter to produce (M+LSF−1) rows of a likelihood image, which in turn would be used to create M rows of spatio-temporally filtered image. Putting all these tricks together can lead to very high efficiencies for computationally heavy systems. However, overheads may become higher for less computationally intense systems, although this is less of an issue. As can be seen from the results, the overheads were made negligible for the higher complexity matched filter based scheme achieving ~24 fps for 1K×1K images, while the lower complexity unsharp masking based scheme achieved only slightly better performance (~27 fps), since it becomes DMA limited, and not computation limited.

Note that with the C6472 device having more than three times the processing power of the C6455, it does a far better job with computationally heavy algorithms. However the data movement speed does not increase proportionally. Therefore, when the scheme described in FIG. 7 is implemented, even with the spatial and temporal filtering merged, the data movement (DMAs) may become the bottleneck. To overcome this roadblock, the processing may be changed to do matched filtering/unsharp masking and spatio-temporal filtering of small sections of the image. This bypasses the need to load to input data twice (once for MF/UM processing and once for STF processing), load the current likelihood image (since it was produced in the previous processing step, and immediately consumed) and the spatial filtered output. The input and previous output image continue to be transferred in by DMAs and the final output and likelihood images continue to be transferred out. This lowers the overall DMA usage and optimizes the overall processing. Table 4 gives the results obtained for such an implementation on a C6472 device compared to a flat memory model simulator. It also provides the frame rate expected for 16-bit 1024×1024 images.

TABLE 4

Performance of algorithms on C64+ cycle accurate simulator (flat memory model)

| Algorithm | Cycles per Pixel on Simulator | Cycles per Pixel on C6455 | Cycles per Pixel on C6472 | Frame rate (1K × 1K images) |
|---|---|---|---|---|
| MF Based Scheme | 168 | 195 | 27.3 | 24 |
| UM Based Scheme | 88 | 104 | 24.8 | 27 |

Thus, multi-step image processing schemes can be mapped to single core and multi-core VLIW architectures. Various implementation aspects like fixed point design, leveraging the available instruction set architecture, cache performance and data transfer and messaging efficiency are disclosed.

A variety of levels of optimization, including optimization at instruction set level, cache and data movement optimization and task scheduling and messaging optimization are illustrated. By considering these aspects, it was shown that even fairly complex algorithms may achieve high frame rates on these single core and multi-core architectures Mapping to a Multi-Core, Floating Point DSP Another embodiment may be implemented on a TMS320C66x core. Unlike the C64x+ core, the C66x core may handle both floating point and fixed point arithmetic. Although the peak processing power for floating point operations is lower than fixed point operations, the peak processing power for fixed point operations of C66x devices is significantly higher than C64x+ based devices. For example, the 8-core C6678 is capable of delivering up to 320 GMacs of processing power, compared to 9.6 GMACs for the single core C6455 and 33.6 GMACs for the six core C6472. This nearly tenfold increase in compute power in these processors will make it possible to implement even more powerful algorithms on these devices. An example of a multi-core floating point DSP is embodied in an SoC from Texas Instruments, and is described in more detail in "TMS320C6678—Multi-core Fixed and Floating-Point Signal Processor Data Manual", SPRS691, November 2010.

The DSP SoCs described herein take a fraction of the power (typically less than tens of watts) consumed by traditional platforms like PCs and general purpose graphic processing units (GPUs). The architecture of DSPs makes them especially well suited for computation intensive tasks allowing most applications, even non data-parallel ones, to efficiently use its resources. The computational bandwidth, low power and small form factor of these devices provides options beyond traditional platforms to system developers. Using these tools system developers could reduce cost or improve performance of existing applications, and open up possibilities for new ones.

Many modifications and other embodiments of the invention will come to mind to one skilled in the art to which this invention pertains having the benefit of the teachings presented in the foregoing descriptions, and the associated drawings. Therefore, it is to be understood that the invention is not to be limited to the specific embodiments disclosed. Although specific terms are employed herein, they are used in a generic and descriptive sense only and not for purposes of limitation.

System Example

Figure 12:
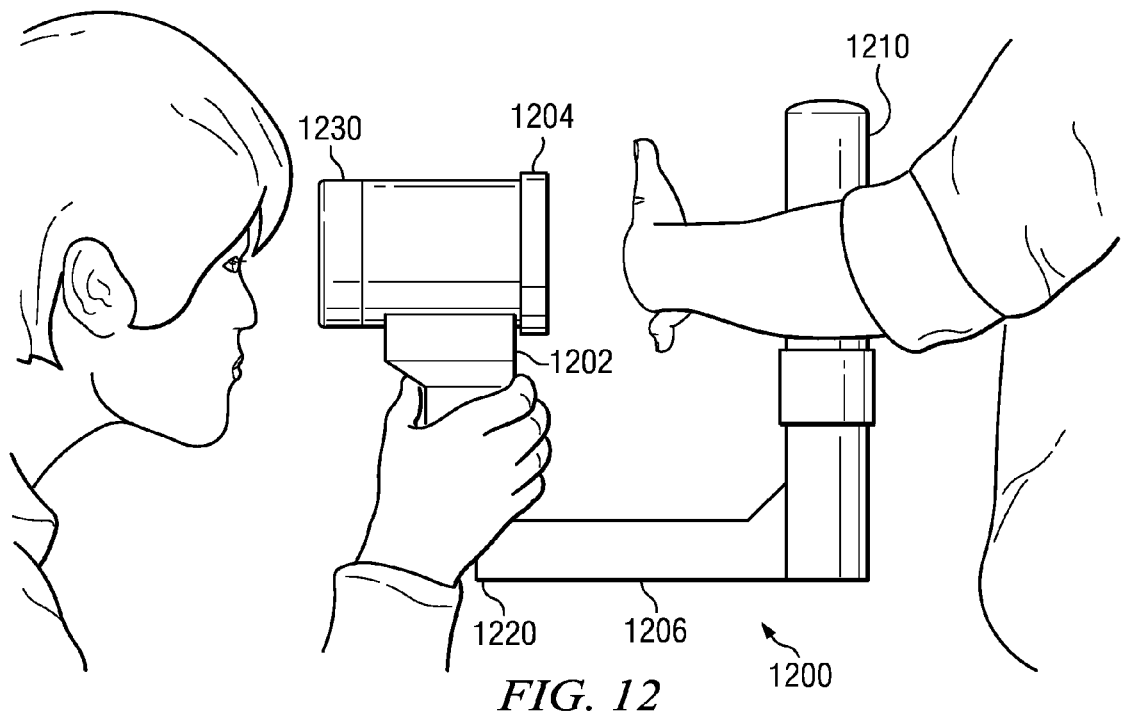
FIG. 12 illustrates a portable fluoroscopy system that includes an embodiment of the present invention.

FIG. 12 illustrates a portable fluoroscopy system 1200 that includes an embodiment of the present invention. This portable system provides real time fluoroscopy results with just a click of its trigger button 1202. A low power microcurrent X-ray tube is positioned within a protective lead shield 1204 so that leakage of X-ray dose to the operator is minimized when in use. A target array 1210 produces digital images in response to the impinging X-ray radiation.

An image processing system 1220 is located within housing 1206 and is connected to receive a stream of digital image frames produced by target array 1210. Image processing system 1220 processes the image stream as described in more detail above to remove noise and improve object identification. The filtered image stream is then displayed on viewing screen 1230 for viewing by a person using the system.

Image processing system 1220 may include a single core or multi-core DSP SoC as previously described herein. A memory subsystem coupled to the DSP is configured to receive the stream of image frames and store them while they are being processed and filtered by the DSP SoC. Programs to perform object identification and spatial and temporal filtering algorithms are stored in a non-volatile memory connected to the DSP SoC that is then loaded into the on-chip memory when system 1200 is turned on. These programs include algorithm modifications and data flow management as described in more detail above to allow all image processing to be performed within a single DSP SoC.

Low power consumption by image processing system 1220 allows portable system 1200 to be battery powered; alternatively, it may be powered from an external source.

Other Embodiments

While the invention has been described with reference to illustrative embodiments, this description is not intended to be construed in a limiting sense. Various other embodiments of the invention will be apparent to persons skilled in the art upon reference to this description. For example, other embodiments of a portable fluoroscopy system may have larger X-ray tubes and be mounted on a cart, table or other support that facilitates easy movement. Other embodiments may be mounted in a fixed location, but still benefit from the low cost and low power operation provided by use of a DSP SoC for image processing. Other embodiments may include one or more monitors or other video display devices for displaying the real-time fluoroscopy sequence to an observer.

In another embodiment, the spatial and temporal filter may use different functions for mapping $\Delta$ than described herein for different types of spatial and temporal filtering that are now known or later developed, as long as the LUT table can be maintained in L1 level memory.

Embodiments of the filters and methods described herein may be provided on any of several types of digital systems: digital signal processors (DSPs), general purpose programmable processors, application specific circuits, or systems on a chip (SoC) such as combinations of a DSP and a reduced instruction set (RISC) processor together with various specialized accelerators. A stored program in an onboard or external (flash EEP) ROM or FRAM may be used to implement aspects of the image signal processing. Analog-to-digital converters and digital-to-analog converters provide coupling to the real world, modulators and demodulators (plus antennas for air interfaces) can provide coupling for waveform reception of image stream data being broadcast over the air by satellite, cellular networks, etc or via wired networks such as the Internet.

The techniques described in this disclosure may be implemented in hardware, software, firmware, or any combination thereof. The software that executes the techniques may be initially stored in a computer-readable medium such as compact disc (CD), a diskette, a tape, a file, memory, or any other computer readable storage device and loaded and executed in the processor. In some cases, the software may also be sold in a computer program product, which includes the computer-readable medium and packaging materials for the computer-readable medium. In some cases, the software instructions may be distributed via removable computer readable media (e.g., floppy disk, optical disk, flash memory, USB key), via a transmission path from computer readable media on another digital system, etc.

Certain terms are used throughout the description and the claims to refer to particular system components. As one skilled in the art will appreciate, components in digital systems may be referred to by different names and/or may be combined in ways not shown herein without departing from the described functionality. This document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" and derivatives thereof are intended to mean an indirect, direct, optical, and/or wireless electrical connection. Thus, if a first device couples to a second device, that connection may be through a direct electrical connection, through an indirect electrical connection via other devices and connections, through an optical electrical connection, and/or through a wireless electrical connection.

Although method steps may be presented and described herein in a sequential fashion, one or more of the steps shown and described may be omitted, repeated, performed concurrently, and/or performed in a different order than the order shown in the figures and/or described herein. Accordingly, embodiments of the invention should not be considered limited to the specific ordering of steps shown in the figures and/or described herein.

It is therefore contemplated that the appended claims will cover any such modifications of the embodiments as fall within the true scope and spirit of the invention.

What is claimed is:

1. A method for performing real-time fluoroscopy image sequence processing in a fluoroscopy system, the method comprising:
    loading at least a first image frame of the fluoroscopy image sequence into an upper level memory of a hierarchical memory system that is coupled to at least one processing core, wherein the hierarchical memory system comprises at least the upper level memory and an L1 level memory having a faster access time than the upper level memory;
    processing the first image frame with an object detection filter to form a likelihood image frame;
    spatially filtering the first image frame with the likelihood image frame using a spatial filter look up table (LUT) employing a single 1-parameter stored in the L1 level memory; and
    temporally filtering the spatially filtered image frame using a temporal filter LUT stored in the L1 level memory,
    wherein the coefficients of the spatial filter are derived with employment of coefficients of the likelihood image.

2. The method of claim 1, wherein the temporal filter LUT is also the spatial filter LUT.

3. The method of claim 1, wherein each pixel of the first image frame has an intensity value, $\Delta$ is a difference in pixel intensity values, z is a scaled difference in intensity values, and wherein the spatial LUT implements a function LUT (z)=1/1+exp(z), where z is a function of $\Delta$, for less than all of the possible values of z, such that the spatial LUT has a size that is less than the size of the L1 level memory.

4. The method of claim 3, wherein $z=-\gamma(\Delta-\beta)$, wherein $\gamma$ specifies a gradient and $\beta$ specifies a horizontal shift.

5. The method of claim 4, wherein for spatially filtering, $\Delta$ is a difference between a pixel intensity in the likelihood image and a neighboring pixel intensity in the likelihood image; and wherein for temporal filtering, $\Delta$ is a difference between a pixel intensity in a current likelihood image and a previous likelihood image at a same coordinate.

6. The method of claim 1, wherein the LUT in the L1 memory level is accessed by the at least one processing core without incurring a wait state.

7. The method of claim 1, wherein the upper level memory is coupled to a plurality of processing cores, wherein a separate L1 level memory is coupled to each of the plurality of processing cores, and wherein a copy of the spatial filter LUT is stored in two or more of the L1 level memories.

8. The method of claim 1, wherein spatially filtering a portion of the first image produces a portion of a spatially filtered image and stores it in the L1 level memory, and wherein temporally filtering uses the spatially filtered image portion in the L1 level memory; and
    repeating spatially filtering and temporally filtering additional portions of the first image until the first image frame is completely filtered.

9. A fluoroscopy system, comprising:
    an X-ray tube configured to provide X-ray radiation to an image array;
    a real-time image processing system coupled to receive a real-time fluoroscopy image sequence from the image array, wherein the real-time image processing system comprises at least one processor core coupled to an L1 level memory and to an upper level memory, wherein the L1 level memory is configured to be accessed by the one processor core with zero wait states, wherein the real-time image processing system is configured to:
        load at least a first image frame of the fluoroscopy image sequence into the upper level memory,
        process the first image frame with an object detection filter to form a likelihood image frame;
        spatially filter the first image frame with the likelihood image frame using a spatial filter look up table (LUT) employing a single 1-parameter stored in the L1 level memory; and
        temporally filtering the spatially filtered image frame using a temporal filter LUT stored in the L1 level memory,
    wherein the coefficients of the spatial filter are derived with employment of coefficients of the likelihood image.

10. The system of claim 9, wherein the temporal filter LUT is also the spatial filter LUT.

11. The system of claim 9, wherein each pixel of the first image frame has an intensity value, $\Delta$ is a difference in pixel intensity values, z is a scaled difference in intensity values, and wherein the spatial LUT implements a function LUT (z)=1/1+exp(z) for less than all of the possible values of z (where z is a function of $\Delta$), such that the spatial LUT has a size that is less than the size of the L1 level memory.

12. The system of claim 11, wherein $z=-\gamma(\Delta-\beta)$, wherein $\gamma$ specifies a gradient and $\beta$ specifies a horizontal shift.

13. The system of claim 12, wherein for spatially filtering, $\Delta$ is a difference between a pixel intensity in the likelihood image and a neighboring pixel intensity in the likelihood image; and wherein for temporal filtering, $\Delta$ is a difference between a pixel intensity in a current likelihood image and a previous likelihood image at a same coordinate.

14. The system of claim 9, wherein the LUT in the L1 memory level is accessed by the at least one processing core without incurring a wait state.

15. The system of claim 9, wherein the upper level memory is coupled to a plurality of processing cores, wherein a separate L1 level memory is coupled to each of the plurality of processing cores, and wherein a copy of the spatial filter LUT is stored in two or more of the L1 level memories.

16. The system of claim 9, wherein the processor core is a digital signal processor.

17. The system of claim 9, being packaged as a portable system.

18. The system of claim 1, wherein a whole real-time fluoroscopy image is computed within a single DSP.

19. The system of claim 9, wherein a whole real-time fluoroscopy image is computed within a single DSP.

\* \* \* \* \*